(12) United States Patent
Mayeaux

(10) Patent No.: US 7,617,745 B1
(45) Date of Patent: Nov. 17, 2009

(54) PORTABLE INSERTABLE PROBE ASSEMBLY

(75) Inventor: Donald P. Mayeaux, St. Amant, LA (US)

(73) Assignee: A+ Manufacturing, LLC, Gonzales, LA (US)

( * ) Notice: Subject to any disclaimer, the term of this patent is extended or adjusted under 35 U.S.C. 154(b) by 0 days.

(21) Appl. No.: 12/325,218

(22) Filed: Nov. 30, 2008

Related U.S. Application Data

(62) Division of application No. 11/151,186, filed on Jun. 13, 2005, now Pat. No. 7,472,615.

(60) Provisional application No. 60/646,332, filed on Jan. 24, 2005.

(51) Int. Cl.
*G01M 19/00* (2006.01)
(52) U.S. Cl. ................................ 73/866.5
(58) Field of Classification Search ............ 73/866.5
See application file for complete search history.

(56) References Cited

U.S. PATENT DOCUMENTS

| | | | | |
|---|---|---|---|---|
| 3,158,865 | A | * | 11/1964 | McCorkle ............ 343/709 |
| 3,691,846 | A | * | 9/1972 | Ingold ............ 73/866.5 |
| 3,831,953 | A | | 8/1974 | Leibfritz et al. ............ 277/180 |
| 3,835,710 | A | * | 9/1974 | Pogorski ............ 73/864.74 |
| 4,014,216 | A | | 3/1977 | Thornton et al. ............ 73/863.23 |
| 4,047,103 | A | * | 9/1977 | Day et al. ............ 376/245 |
| 4,112,768 | A | | 9/1978 | Holland et al. ............ 73/863.24 |

(Continued)

FOREIGN PATENT DOCUMENTS

JP 6-288880 10/1994 ............ 73/863

(Continued)

OTHER PUBLICATIONS

A+ Corporation, "Series 100 Genie Membrane Separators", Aug. 1998, pp. 1-7.*

(Continued)

*Primary Examiner*—Thomas P Noland
(74) *Attorney, Agent, or Firm*—Joseph T. Regard, Ltd plc

(57) ABSTRACT

An assembly for insertion and retraction of probe or probe-like device which does not require a seal or packing gland, instead utilizing pressure equalization between pressurized process fluids and the housing containing a probe, so as to negate the use of a dynamic seal. The preferred embodiment of the present invention contemplates an inserting/retraction mechanism for raising and lowering the probe into and from the pressurized fluid, respectively. A housing having a valve is configured to allow fluid communication between the pressurized fluid source, and the interior of the housing assembly. A conduit engages the housing assembly, and is formed to slidingly receive the outer diameter of the probe therethrough, such that a sliding seal maintains a fluid seal between the outer wall of the probe and the inner wall of the conduit, as the probe is telescoped therethrough during insertion and retraction of the probe into/from the pressurized process. Fluid flow will occur until the pressure of the housing assembly and the fluid source are equal to each other. The probe is then lowered through an opening in the first end of the housing assembly without having to overcome the force exerted by the differential pressure across a dynamic seal. An example of the insertion/retraction mechanism of the present invention utilizes a rack and pinion system.

15 Claims, 7 Drawing Sheets

U.S. PATENT DOCUMENTS

| | | | | |
|---|---|---|---|---|
| 4,157,040 | A | | 6/1979 | Barton et al. ............ 73/863.23 |
| 4,166,481 | A | * | 9/1979 | Farris et al. ..................... 141/1 |
| 4,630,492 | A | * | 12/1986 | Goode ..................... 73/863.82 |
| 4,800,763 | A | | 1/1989 | Hakkers et al. ............... 73/863 |
| 4,821,585 | A | | 4/1989 | Kempe ................... 73/863.23 |
| 4,865,811 | A | | 9/1989 | Newton et al. ................ 422/81 |
| 4,928,541 | A | | 5/1990 | Toon et al. .............. 73/864.63 |
| 5,076,108 | A | * | 12/1991 | Trimarchi ................. 73/866.5 |
| 5,205,988 | A | | 4/1993 | Tanaka et al. ................. 422/91 |
| 5,442,969 | A | * | 8/1995 | Troutner et al. ....... 73/863.85 X |
| 5,619,043 | A | * | 4/1997 | Preikschat et al. .......... 250/574 |
| 5,637,792 | A | | 6/1997 | Kimura et al. ................ 73/116 |
| 5,814,741 | A | | 9/1998 | Wang et al. .............. 73/863.12 |
| 5,815,264 | A | * | 9/1998 | Reed et al. .................. 356/336 |
| 5,844,123 | A | | 12/1998 | Marsh et al. .......... 73/863.12 X |
| 2003/0152493 | A1 | * | 8/2003 | Lefebvre ................... 422/100 |

FOREIGN PATENT DOCUMENTS

WO 95/02176 1/1995

OTHER PUBLICATIONS

Natural Gas Samples for Custody Transfer, API (4th Ed, Aug. 1993), pp. 2, 3, 6, and 12.
Technical Memorandum—Metering Research Facility Program; Gas Research Institute, Transmission Operations, Apr. 1998, pp. 32-33.
The Calibration Station (Newsletter of Colorado Engineering Experiment Station, Inc.) vol. 1, Fall Winter 1997, pp. 1-2.
Welker, Thomas F., Sample Conditioning, 1997 Proceedings of AM SCH of Gas Measurement Tech, pp. 79-81.
Ting, V.C., Effect of Entrained Liquid on Orifice Measurement, Sep. 1998, Proceedings of AM Sch of Gas Measurement Tech, pp. 85-88.
A+ Corp, Prairieville, LA Series 100 Genie Membrane Separators Brochure, Rev Aug. 1998, pp. 1-7.
A+ Corp, Prairieville, LA Series 200 Genie Membrane Separators Brochure, Rev Mar. 1996, pp. 1-6.

* cited by examiner

PORTABLE INSERTABLE PROBE ASSEMBLY

The present application is a Divisional of patent application Ser. No. 11/151,186 filed Jun. 13, 2005 now U.S. Pat. No. 7,472,615 entitled "Portable Insertable Probe Assembly", which claims the benefit of Provisional Application 60/646,332 filed Jan. 24, 2005 entitled "Portable Insertable Probe Assembly".

TECHNICAL FIELD OF THE INVENTION

The present invention relates to the insertion of a probe into a pressurized process. Insertion of a probe into a pressurized process is often required for the purpose of extracting fluid samples, measuring fluid temperature, insertion of corrosion coupons and many other uses.

The preferred embodiment of the present invention contemplates a system configured to insert a probe though the sidewall of a containment vessel, whereas a pressure equalization technique is utilized in lieu of a probe packing gland or seal. Safety is improved by eliminating potential seal leaks. The length and size of the assembly is smaller than current means, the complexity of operation is reduced, and the overall cost for fabrication is reduced.

BACKGROUND OF THE INVENTION

The heating value of natural gas has a significant impact on its monetary value. In general, the heating value of natural gas increases as the concentration of low volatility, high molecular weight components increases. Condensation of gas phase components, which reduce the proportion of high molecular weight components, therefore tends to decrease gas phase heating value, while vaporization of entrained liquid has the opposite effect.

In order for natural gas supply to keep up with demand over the next 10 to 20 years, it will be necessary to increase production from deep-water fields in the Gulf of Mexico. (Refer to Volume 1, Fall/Winter 1997 official newsletter of Colorado Engineering Experiment Station Inc.) Gas produced from deep-water fields contains higher concentrations of low volatility components, such as water vapor and heavy hydrocarbons, and has a higher susceptibility to condensation than shelf and onshore production gas.

Additionally, some onshore produced gas, particularly in low ambient temperature regions, frequently contains entrained liquids. Other liquids, which can influence vapor phase composition when fluid pressure or temperature changes occur, include glycols and amines, which are carried over into the gas phase from gas contactors designed to remove water vapor and acid gases, respectively.

A Joint Industry Project (JIP) is underway to address problems associated with measurement and transportation of wet gases. A part of the JIP focus will include improvement of wet gas sampling techniques.

The American Petroleum Institute (API) and the Gas Processors Association (GPA) are two leading industry organizations, having recommended standard practices for sampling and analysis of natural gas.

Both of these organizations recommend the use of sample probes inserted into the process fluid, for the purpose of extracting samples of said process fluids. Further, both require that the probe be inserted to a specific depth in the containment vessel or pipeline. (Refer to Manual of Petroleum Measurement Standards Chapter 14—Natural Gas fluids measurement, section 1 collecting and handling natural gas samples for custody transfer, fourth edition, August 1993.)

Insertion of probes into pressurized systems for collecting liquid samples is also a frequent requirement.

In many cases, the cost of installing a fixed probe at each sample location is cost prohibitive. For example, some pipeline companies sample fluids at several thousand locations. Outfitting each sample tap location could cost several million dollars. The result is that fluids are often sampled without the use of probes, which results in non-conformance of applicable standards, and inaccurate sample analysis.

It is desirable, therefore, to have the capability of inserting a probe into the pressurized fluid systems at the time of sampling, and retracting said probe upon the completion of the sampling process. To be effective, the probe insertion/retraction process must be safe, easy and quick to perform, portable, and effective for the intended service.

The same can be said for measuring the fluid temperature, wherein a temperature probe or well designed to receive a temperature probe is required to be inserted and/or retracted from a pressurized fluid stream or containment vessel. There is also a frequent need to insert other types of devices into pressurized system, such as the insertion/retraction of corrosion coupons, flow measuring devices and various types of sensors, analyzer, and devices.

Additionally, it is often desirable to retract a probe-type of device from a pressurized system to accommodate 'pigging', or other type of maintenance operation.

Insertion and retraction devices for insertion/retraction of probe or probe like devices are known. However, they all employ a seal, through which the probe is inserted into the pressurized system, for the purpose of preventing pressurized fluid from leaking. In these probes, the insertion force is derived either from a screw-type of device, or pneumatically or hydraulically. Such is the case with U.S. Pat. Nos. 4,177,676, 5,770,809, 5,639,975 and 5,627,749. The apparatus of these aforementioned patents are bulky and long, requiring, at a minimum, a length of at least twice the maximum insertion length to extend above the point of insertion into a vessel. In many cases, such as in the tight quarters of a chemical plant, refinery, or offshore drilling platform, the bulk and length of these type devices preclude their use.

SUMMARY OF INVENTION

Unlike the prior art, the present invention provides an assembly for insertion and retraction of a probe or probe-like device which does not require a seal or packing gland. For a given insertion/retraction length, the required insertable probe assembly length is considerably less than that of prior art devices, and since dynamic sealing of the probe which is known to leak fluids is not required with the present invention, safety is enhanced.

The preferred embodiment of the present invention contemplates pressure equalization between the pressurized process fluids and the housing containing a probe, so as to negate the use of a dynamic seal. In a first operating mode of the preferred embodiment of the present invention, the housing assembly, having a first and second end and containing the probe, has its first end attached, and in fluid communication with, the pressurized source fluid, through a full opening valve. Said attachment is by means of threads, flange, or other similar means.

Said valve is opened so as to allow fluid communication between the pressurized fluid source, and the interior of the housing assembly. Fluid flow will occur until the pressure of the housing assembly and the fluid source are equal to each other. The probe can now be lowered through an opening in the first end of said housing assembly without having to overcome the force exerted by the differential pressure across a dynamic seal, as is the case with prior art.

This allows for relatively simple means of inserting/retraction of the probe into and from the pressurized fluid. A preferred means of the preferred embodiment of the present invention for insertion/retraction is the use of the rack and pinion, wherein the rack in fabricated on the probe and the pinion, anchored in the housing assembly, is rotated manually.

In the preferred embodiment, the housing assembly has a first end attached and in fluid communication with the pressurized fluid source. When a first end of the probe is inserted into the pressurized fluid source, a second end of the probe remains within the housing assembly. In the preferred embodiment, a conduit having a first and second end is contained within the housing assembly.

The second end of said conduit is attached, and fluidly sealed to, the inner wall of the second end of said housing assembly. The inner diameter of the conduit is larger than the outer diameter of the probe. The first end of the probe extends inside the conduit. A sliding seal is established between the inner wall of the conduit and the outer wall of the probe. This allows the interior space of the probe and conduit to maintain fluid isolation with the space interior to the housing assembly, and exterior to the probe and conduit.

This arrangement of the probe and conduit provides a telescoping action, as the first end of the probe is inserted into, and retracted from, the pressurized process. Said sliding seal maintains a fluid seal between the outer wall of the probe and the inner wall of the conduit, during the telescoping process. The second end of said conduit is attached to, and fluidly sealed to, the interior wall of the second end of the housing assembly. An outlet port, permitting external fluid communication with the interior of the second end of said conduit, is formed in the second end of the housing assembly.

Therefore, when the probe housing assembly is attached to a pressurized fluid pressure source through a fully opening valve, the probe can be manually inserted to a desired depth in the pressurized fluid source, thereby providing a fluid path between said pressurized source and said outlet port.

It should be noted that since a seal does not exist between the outer probe wall and the interior wall of the housing assembly, the pressure internal to the housing assembly, but external to the probe and conduit, is essentially the same as the static pressure of the pressurized fluid source.

It should also be noted that the internal pressure of the probe and conduit are also essentially the same, as the static pressure of the pressurized fluid source, with only a slight difference existing whenever fluid flow through the probe and conduit cause a slight pressure drop.

The differential pressure across said sliding seal is minimal. In a second embodiment, fluid communication between the second end of the probe and the outlet port is by way of a flexible conduit attached to and in fluid communication between the second end of said probe and said outlet port. In this second embodiment, the conduit and sliding seal are eliminated.

In the preferred embodiment, by closing off the first end of said probe, a well is formed interior to the probe, with the conduit extending from the outlet port to the first end of said probe. Said well can be at atmospheric pressure when the outlet port is opened to the atmosphere, and can therefore be utilized for several purposes, such as, for inserting a temperature sensor inside of the pressurized fluid source.

Other minor variations obvious to one skilled in the art are also possible, such as insertion/retraction of corrosion coupons, or various sensors inside of the pressurized fluid process. Another variation of the preferred embodiment of the probe housing assembly is for the first end of the probe to slide over the first end of the conduit, wherein the sliding seal is formed between the inner wall of the first end of the probe, and the outer wall of the conduit.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein.

DETAILED DISCUSSION OF THE INVENTION

Figure 1:
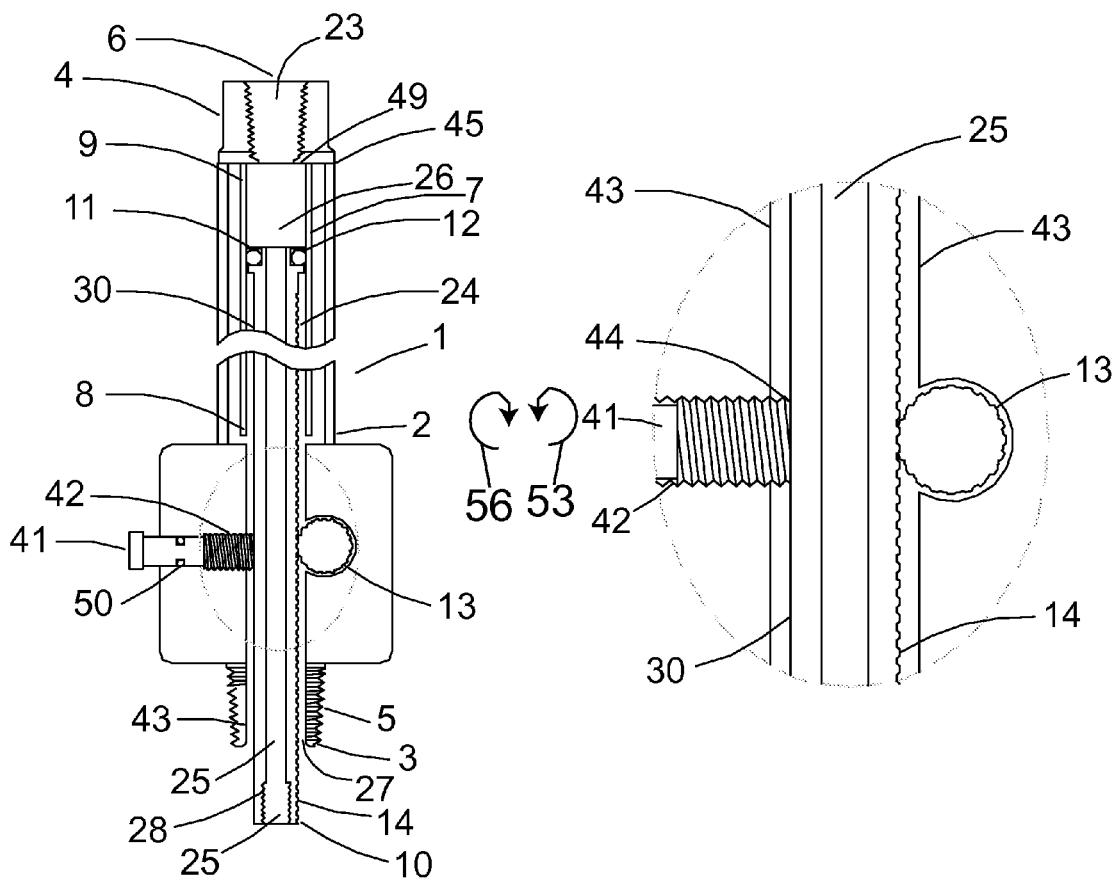
FIG. 1 is a side, partially cut-away view of the preferred first embodiment of the invention illustrating the probe house assembly.
Figure 2:
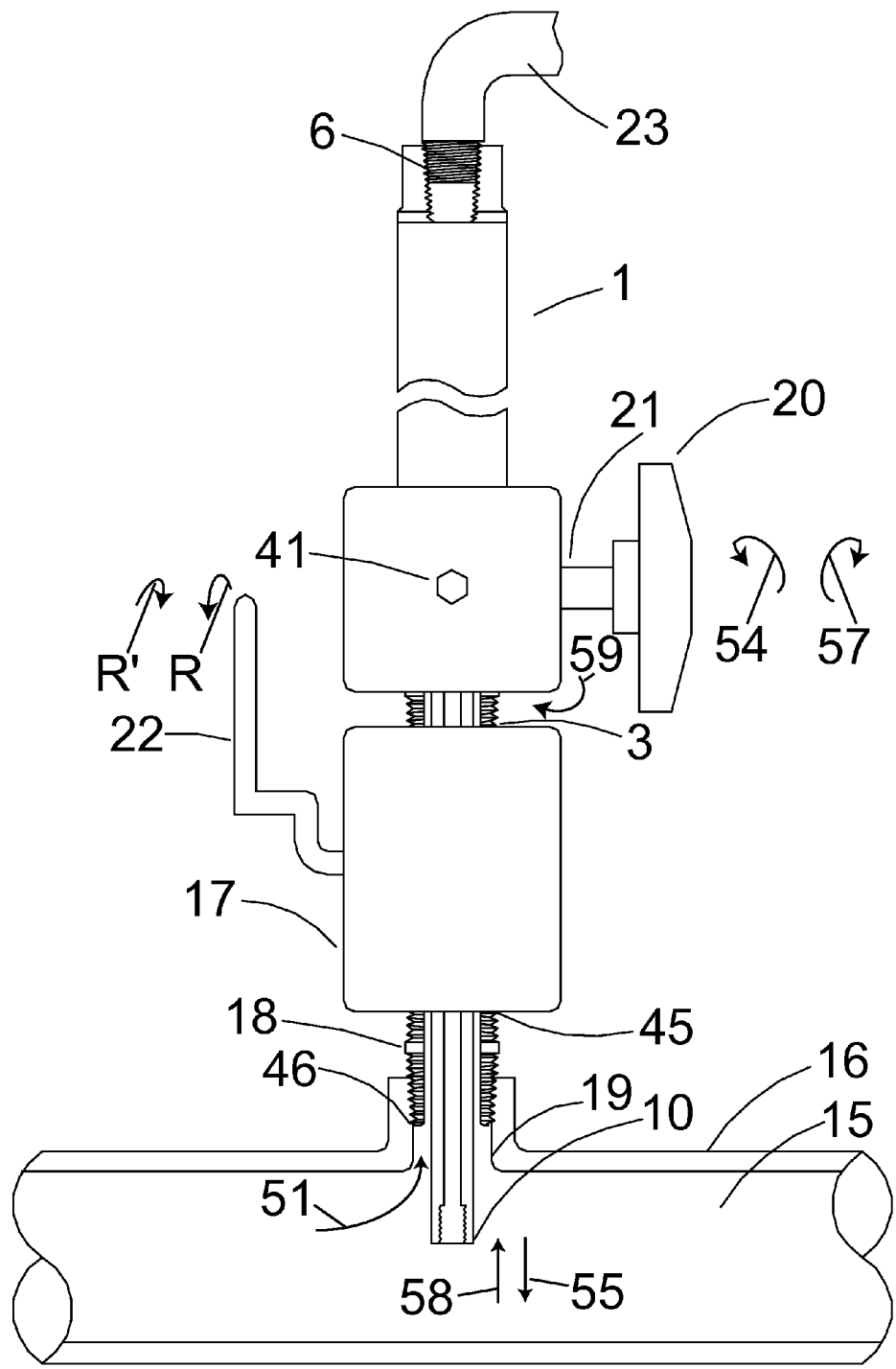
FIG. 2 is a side, partially cut-away view of the preferred first embodiment of FIG. 1 in an exemplary installation.

Referring to FIGS. 1 and 2, the preferred first embodiment of the invention contemplates a probe housing assembly 1 comprising a probe 30, conduit 7, and housing assembly 2. Cavity A 24, formed within housing assembly 2, extends longitudinally from the first end 3 of housing assembly 2 to the second end 4 of housing assembly 2. Cavity A 24 is formed between the inner wall 43 of housing assembly 2, and is external to conduit 7. Threaded outlet port 6 is formed in the second end 4 of housing assembly 2, and male NPT threads 5 are formed in first end 3 of housing assembly 2.

The second end 9 of conduit 7 is attached and fluidly sealed to the inner wall 49 of the second end 4 of housing assembly 2. The first end 8 of conduit 7 extends into cavity A 24. Sliding seal 12 is formed on second end 11 of probe 30, said second end 11 of probe 30 being inserted into the open end of first end 8 of conduit 7, said sliding seal 12 providing fluid seal between the outer wall of second end 11 of probe 30 and the inner wall of conduit 7.

A rack gear 14 on probe 30 extends from first end 10 of probe 30 to second end 11 of probe 30, said rack gear 14 mechanically engaged with pinion gear 13 associated with housing 2. Said pinion gear 13 having a pinion gear shaft 21 and pinion gear handle 20 formed to provide an external means for mechanically rotating said pinion gear 13.

Probe travel locking screw 41 threadingly engaged in threaded opening 42 provides a means for locking probe 30 at a desired protrusion length, by selectively rotating the screw to engage or disengage said probe. Seal 50 provides a seal between the atmosphere and the pressure fluid process. Fluid communication passage 23 is established between the first end 10 of probe 30 and threaded outlet port 6, said fluid path comprising of passage A 25, formed internal to probe 30 and passage B 26, formed internal to conduit 7.

Said fluid path is formed to be capable of providing a fluid flow from pressurized fluid process 15 to an external device fluidly attached to threaded outlet port 6. The function of the preferred, first embodiment of the invention is to extract a sample of fluid from a pressurized fluid process 15.

In operation of the preferred first embodiment of invention, probe housing assembly 1 is attached to a fully opening valve 17 by way of male NPT threads 5, said fully opening valve 17 being attached to a first end 45 of nipple 18 and second end 46 of nipple 18 being threadingly attached to pipe or vessel 16. An opening 19 formed in the wall of the pipe or vessel 16 provides fluid communication between nipple 18 and pressurized fluid process 15.

After probe housing assembly 1 is attached to fully opening valve 17 as previously described, said fully opening valve 17 is manually opened by rotating R valve handle 22 wherein a small volume of fluid from pressurized fluid process 15 flows 51 through opening in wall of pipe or vessel 19, annulus 27 and into cavity A 24 until its fluid pressure in cavity A 24 is equal to that of the pressurized fluid process 15. Rotating 53 first end 44 of probe travel locking screw 41 in a counter-clockwise manner will disengage probe travel locking screw from probe, and release probe 30.

Rotating pinion gear handle counterclockwise 54 will extend 55 probe 30 out of housing assembly 2. In this manner probe 30 can be extended through fully opening valve 17, nipple 18, opening in wall pipe or vessel 19 and into pressurized fluid process 15. When first end 10 of probe 30 is extended to the desired depth in pressurized fluid process 15, rotating 56 probe travel locking screw 41 in a clockwise manner until it is securely against probe 30 will engage and lock said probe 30 in that position. During the extension of probe 30, sliding seal 12 maintains a fluid seal between cavity A 24 and passages A 25 and passage B 26.

To detach the probe housing assembly from the fully opening valve 17, one must first unlock probe 30 by turning or rotating 53 probe travel locking screw 41 counter-clockwise to disengage, rotate 57 pinion gear handle 20 clockwise until probe 30 is fully retracted 58 into housing assembly 2, turning or rotating 56 probe travel locking screw 41 clockwise to engage and lock probe 30 in place, rotate R' valve handle 22 clockwise until fully opening valve 17 is fully closed then unscrewing 59 male NPT threads 5 from the body of fully opening valve 17.

The rack and pinion drive illustrated and discussed is only an example of various means which can be implemented to selectively extend and retract the probe from the housing assembly. A friction drive comprising, for example, a friction wheel rotatingly mounted to the housing and frictionally engaging the probe may likewise be utilized with a handle for selective rotation of the wheel, much in the manner discussed above, could likewise be utilized with good results. Other alternatives could include, for example, magnetic means in the form or electromagnets, rare earth magnets, or the like mounted to the housing or probe to facilitate the selective extension or retraction of the probe from the housing assembly.

Figure 7:
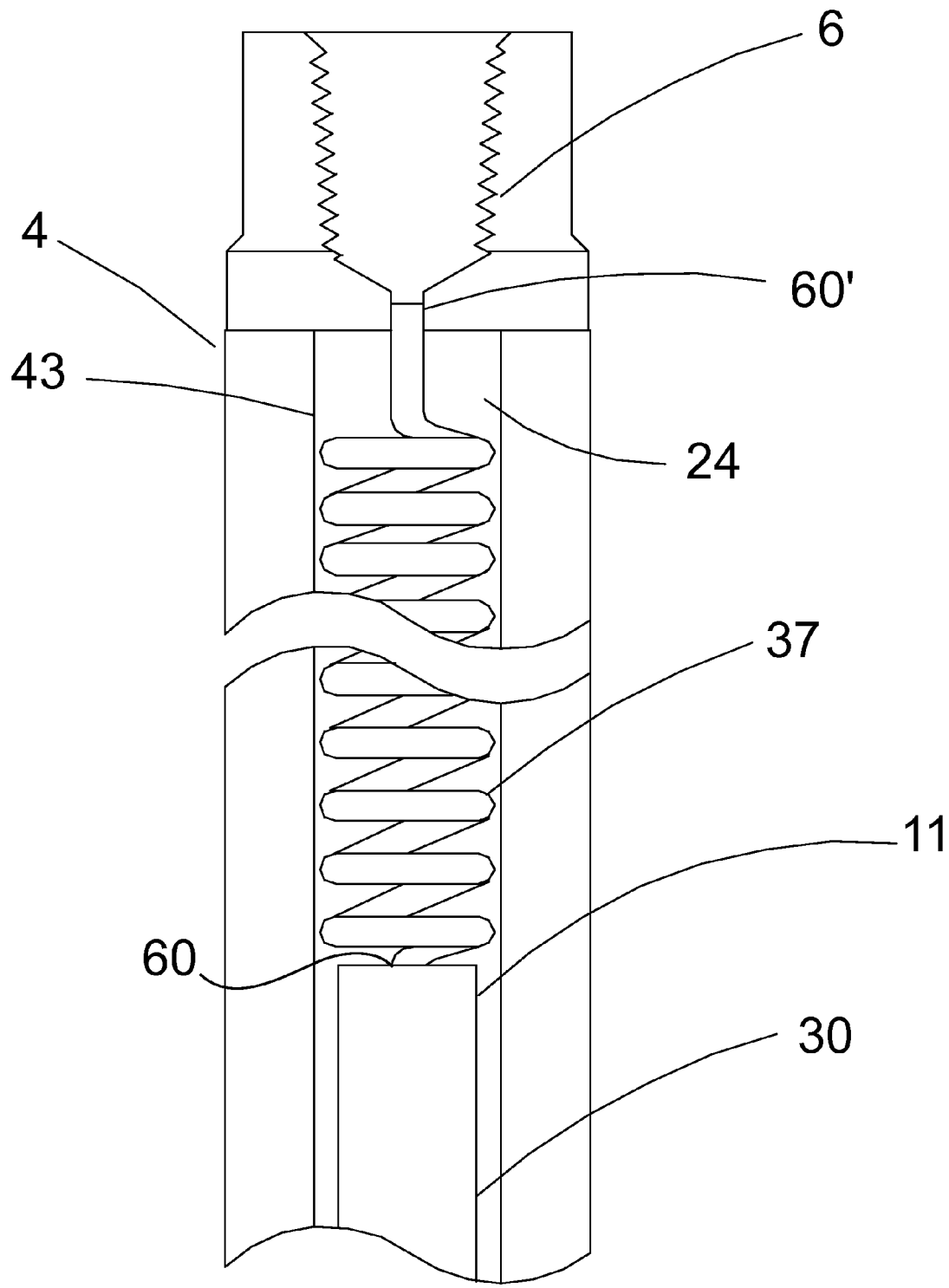
FIG. 7 is a side, partially cut-away view of a second embodiment of the invention, wherein there is shown a flexible conduit for sample fluid extraction from the pressurized fluid process.

In preferred second embodiment of the invention (Refer to FIG. 7), a flexible tube or conduit 37 having first 60 and second 60' ends, shown in a helical coiled configuration, engages the second end 11 of probe and outlet port 6, respectively, to provide fluid communication therebetween. The operation of probe housing assembly 1, for extracting a pressurized fluid process 15 sample, is essentially the same as that of the aforementioned preferred first embodiment.

Figure 3:
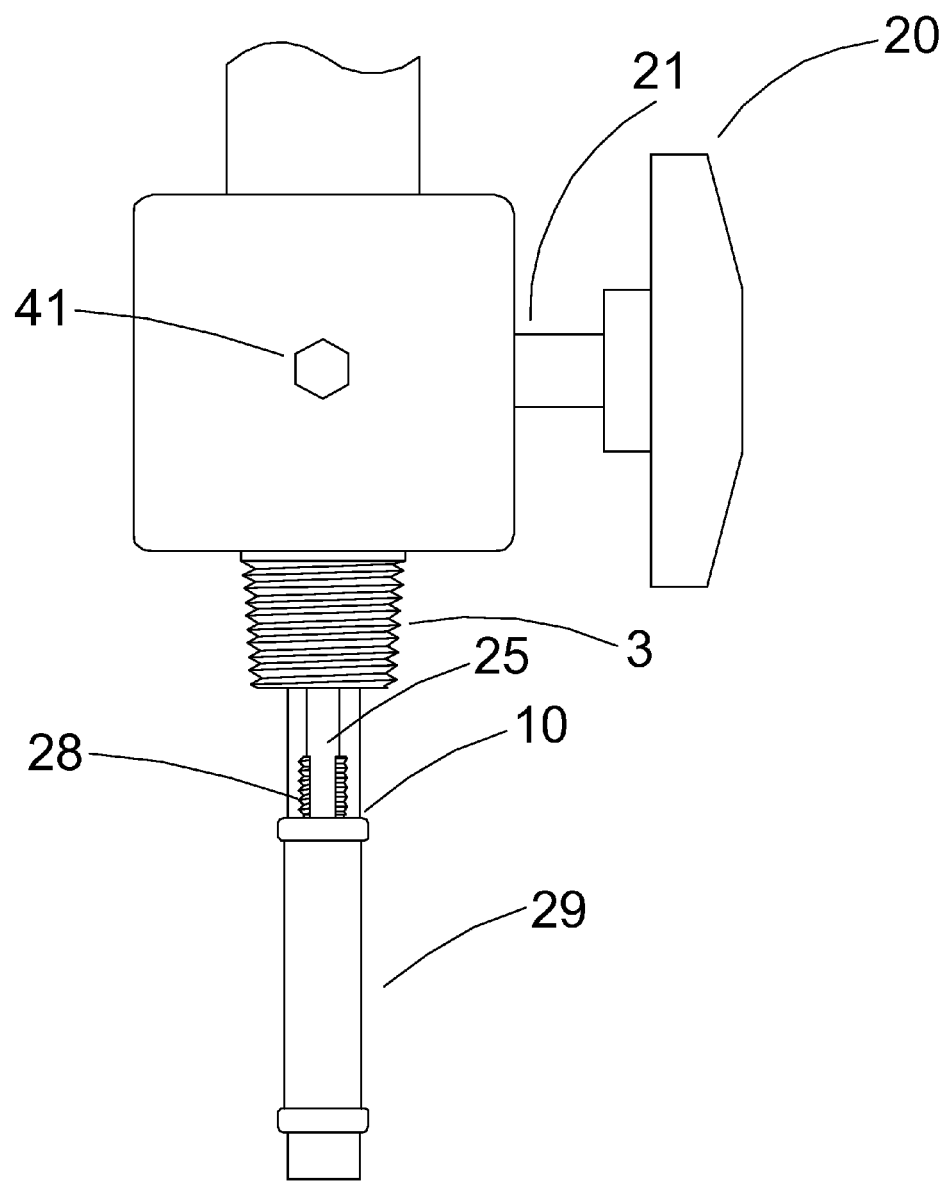
FIG. 3 is a side, partially cut-away view of a third embodiment of the present invention incorporating a phase separating membrane/filter assembly.

In a preferred third embodiment of the invention (Refer to FIG. 3), a phase separating membrane/filter assembly 29 is attached to threaded opening 28 to passage A 25, said phase separating membrane/filter assembly 29 rejecting liquid and solid particles while allowing the passage of gas or vapors into passage A 25. Operation of said third embodiment is essentially as that of first embodiment.

Figure 4:
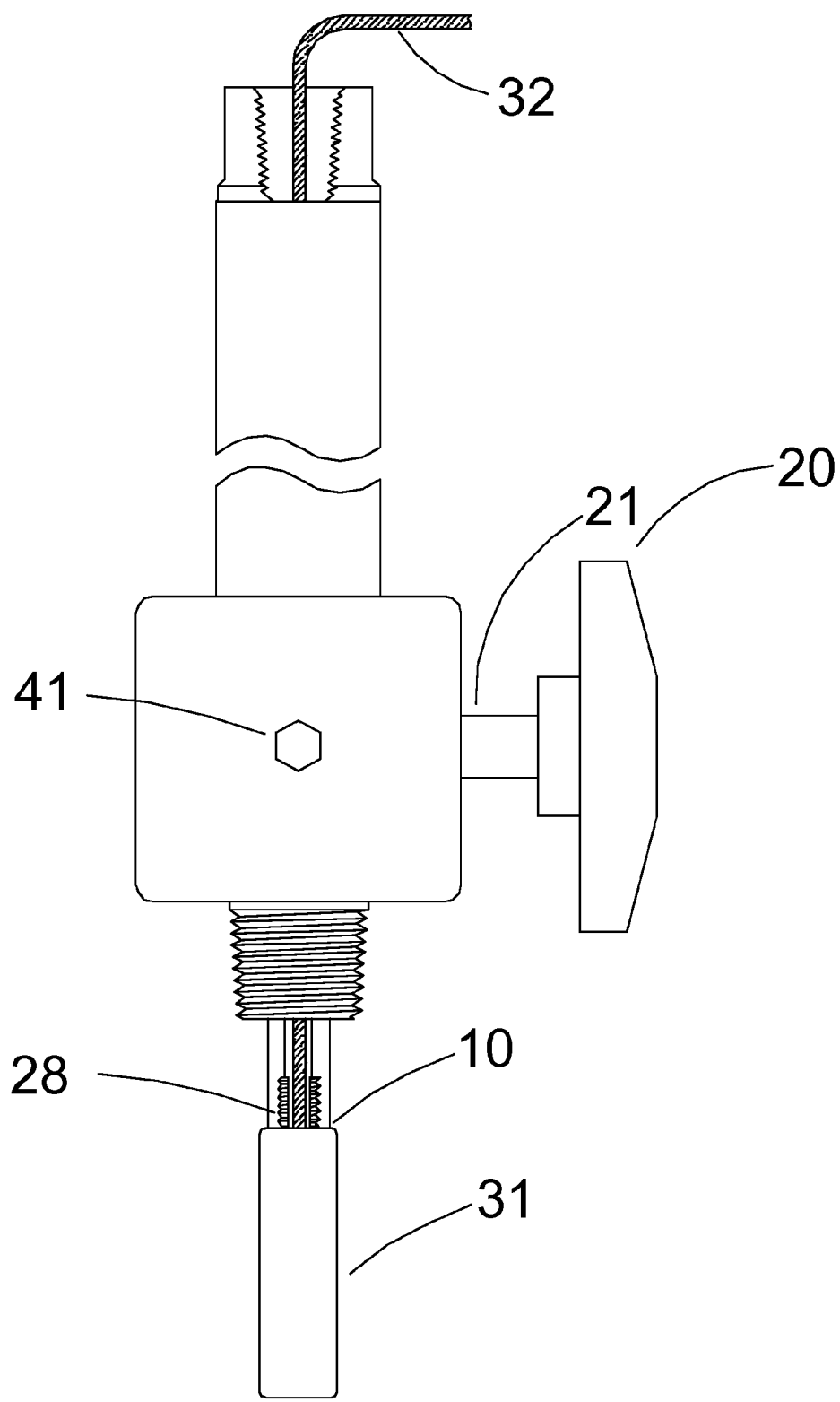
FIG. 4 is a side, partially cut-away view of a fourth embodiment of the present invention, incorporating a sensor for selectively engaging the pressurized fluid process.

In a preferred fourth embodiment of the invention (Refer to FIG. 4) a sensor 31 is attached to threaded opening 28 to passage A 25, said sensor 31 having communication cable 32 extending through passage A 25, passage B, and outlet port 6. Operation for extending sensor 31 into pressurized fluid process 15 is essentially the same as for preferred first embodiment.

Figure 5:
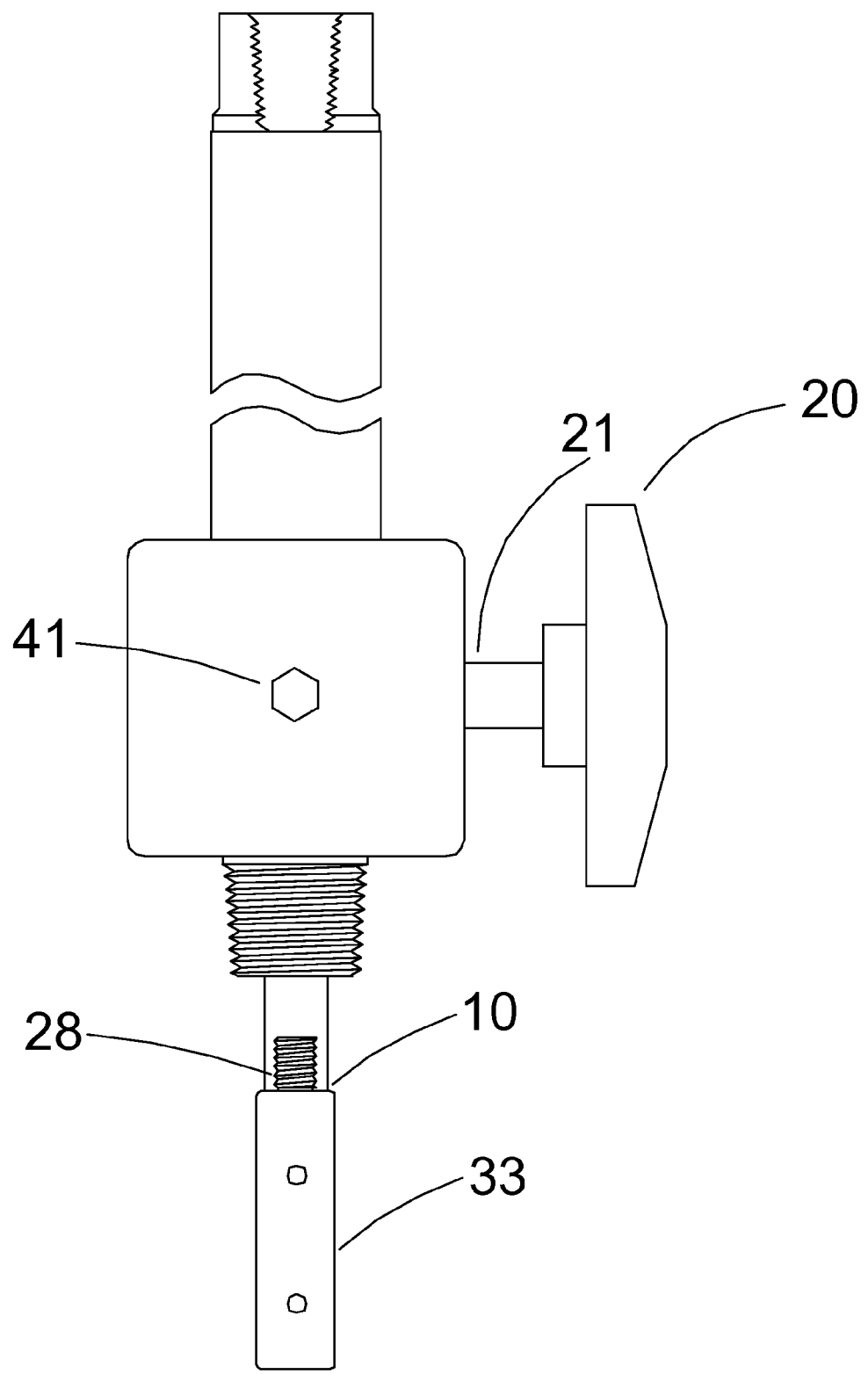
FIG. 5 is a side, partially cut-away view of a fifth embodiment of the present invention wherein there is provided an attachment plate engaging a corrosion coupon for selectively engaging the pressurized fluid process.

In a preferred fifth embodiment shown in FIG. 5 attachment plate for corrosion coupon 33 is attached to threaded opening 28 to passage A 25 which can then be inserted into a pressurized fluid process 15 in a manner similar to that described for first preferred embodiment.

Figure 6:
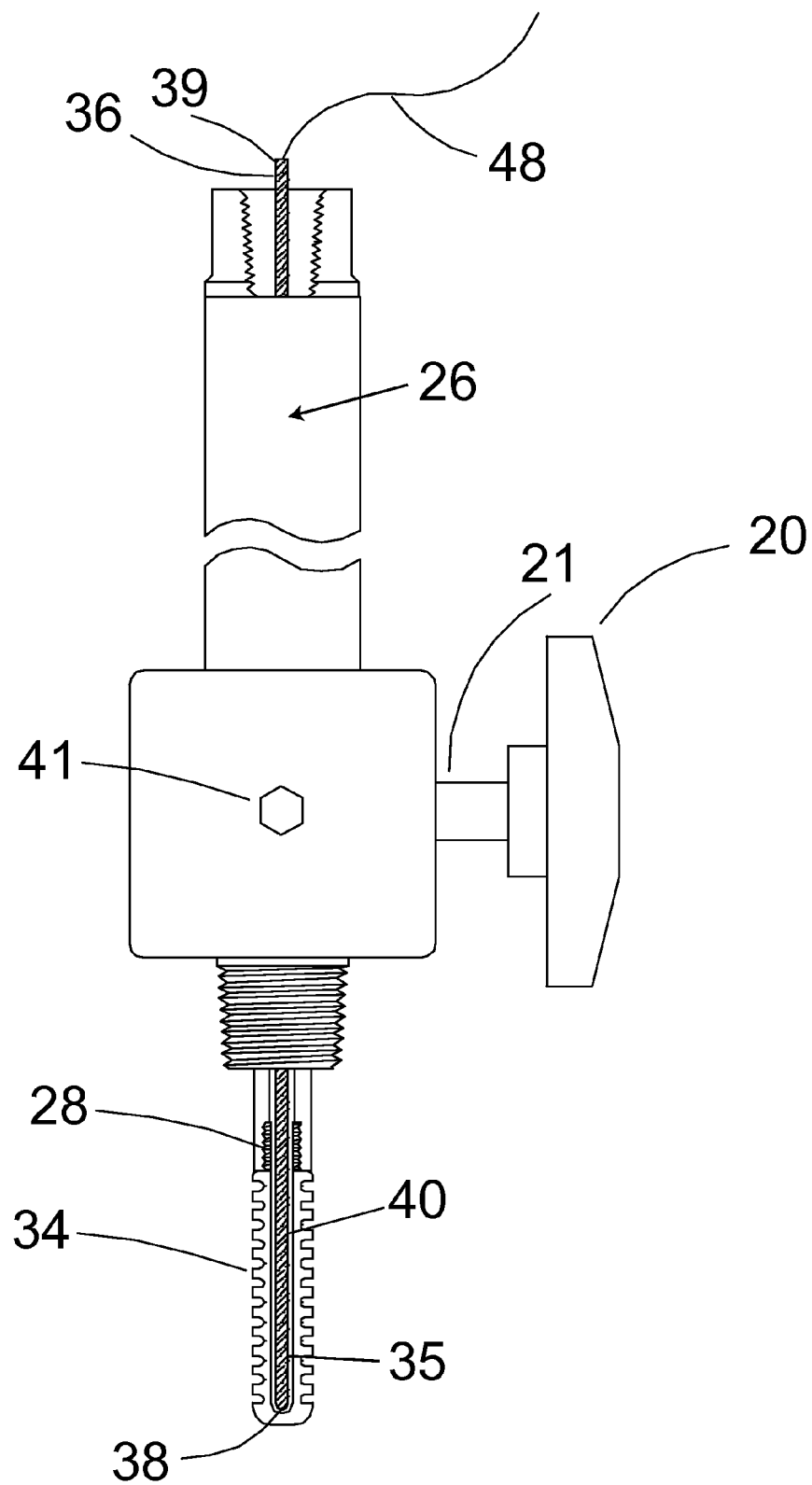
FIG. 6 is a side, partially cut-away view of a sixth embodiment of the invention wherein there is provided a well for receiving a temperature sensor or other object for lowering into a monitoring area.

In a sixth preferred embodiment (Refer to FIG. 6) a closed end cap 34 having a finned outer surface 40 is attached to threaded opening 28 to passage A 25 which effectively seals off said threaded opening 28 to passage A.

Thus, a well is formed, comprised of closed end cap well 35, passage A 25, passage B 26, and threaded outlet port 6. A temperature sensor 36 or other similar object can now be lowered (at its first end 38) into the closed end cap well 35, which remains open to the atmosphere even when probe 30 is extended into pressurized fluid process 15.

A temperature sensor cable 48 relays the signal from the probe at the second end 39 of the temperature sensor 36. Operation of this sixth preferred embodiment is similar to that of the preferred first embodiment. The fins facilitate thermal transfer from said pressurized fluid process to said sensor in said well.

In summary, the method engaging a pressurized fluid system with a probe utilizing the preferred embodiment of the present invention may be summarized as follows:

a. providing a probe housing assembly for insertion and retraction of a probe into a pressurized vessel, comprising:

a telescoping probe having first and second ends, said telescoping probe having an internal fluid passage formed therethrough extending from said first end of said telescoping probe to said second end of said telescoping probe;

a housing having first and second ends, said housing having an internal cavity formed therethrough extending from said first end of said housing to said second end of said housing, said housing formed to engage, in a fluidly sealed manner, a pressurized fluid process in said pressurized vessel;

said telescoping probe slidingly disposed in said internal cavity formed in said housing in an approximate coaxial relationship with said housing, such that said second end of said telescoping probe can engage, in a fluidly sealed manner, said second end of said housing;

b. engaging said first end of said housing to valve engaging a pressurized vessel containing a pressurized fluid process;

c. opening said valve, providing an opening;

d. allowing said pressurized fluid process to selectively pass through said opening in said valve and into said internal cavity formed in said housing;

e. extending said first end of said probe from said housing, through said open valve, into said pressure vessel, such that said first end of said probe engages said pressurized fluid process;

f. retracting said probe into said housing, and g. closing said valve.

With the above process, a fluid sample can be obtained or other function accomplished, including, for example:

utilizing the fourth embodiment of the invention, mounting a sensor to said first end of said probe would allow one to expose said sensor to said pressurized fluid process in step "e".

utilizing the sixth embodiment of the invention, mounting a closed end cap having a cavity to said first end of said probe such that said cavity of said closed end cap communicates with said passage formed in said probe, to provide a well, would allow one, in step "e" to lower a sensor into said well while said well remains at atmospheric pressure with said probe engaging said pressurized vessel to seal said well from said pressurized fluid process, allowing said sensor to analyze said pressurized fluid process, while remaining at atmospheric pressure.

utilizing the preferred embodiment of the present invention, in step "e" one could of allow said pressurized fluid process to flow into said conduit formed in said probe, sampling said pressurized fluid process, providing sampled fluid.

utilizing the second embodiment of the invention, in step "e", one could utilize directly said sampled fluid through said flexible conduit, through the outlet port of said housing assembly, for collection.

utilizing the third embodiment of the present invention, in step "e" one could utilize said phase separating membrane/filter assembly to engage said pressurized process fluid such that gas flows through said phase separating membrane/filter assembly into said conduit formed in said probe, while rejecting liquid and solid particles flowing through said pressurized process fluid, and utilizing the fifth embodiment of the present invention, in step "e", one could expose said corrosion coupon to said pressurized fluid process, for analysis of same.

RECITATION OF THE ELEMENTS OF THE INVENTION

1. Probe housing assembly
2. Housing assembly
3. First end of housing assembly
4. Second end of housing assembly
5. Male NPT threads
6. Threaded outlet port
7. Conduit
8. First end of conduit
9. Second end of conduit
10. First end of probe
11. Second end of probe
12. Sliding seal
13. Pinion gear
14. Rack gear
15. Pressurized fluid process
16. Pipe or vessel
17. Fully opening valve
18. Nipple
19. Opening in wall of pipe or vessel
20. Pinion gear handle
21. Pinion gear shaft
22. Valve handle
23. Fluid communication passage
24. Cavity A
25. Passage A
26. Passage B
27. Annulus
28. Threaded opening to passage A
29. Phase separating membrane/filter assembly
30. Probe
31. Sensor
32. Sensor cable
33. Attachment plate for corrosion coupon
34. Closed end cap
35. Closed end cap well
36. Temperature sensor
37. Flexible conduit
38. First end of temperature sensor
39. Second end of temperature sensor
40. Finned outer surface
41. Probe travel locking screw
42. Threaded opening
43. Inner wall of housing assembly
44. First end of probe travel locking screw
45. First end of nipple
46. Second end of nipple
47. Second end of conduit
48. Temperature sensor cable
49. Inner wall of second end of housing assembly
50. Seal
51. Flows
52.
53. Rotating
54. Rotating
55. Extended
56. Rotating
57. Rotating
58. Unscrewed The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What is claimed is:

1. The method of engaging a pressurized fluid system with a probe, comprising the steps of:

a. providing a probe housing assembly for insertion and retraction of a probe into a pressurized vessel, comprising:

a telescoping probe having first and second ends, said telescoping probe having an internal fluid passage formed therethrough extending from said first end of said telescoping probe to said second end of said telescoping probe;

a housing having first and second ends, said housing having an internal cavity formed therethrough extending from said first end of said housing to said second end of said housing, said housing formed to engage, in a fluidly sealed manner, a pressurized fluid process in said pressurized vessel;

said telescoping probe slidingly disposed in said internal cavity formed in said housing in an approximate coaxial relationship with said housing, such that said second end of said telescoping probe can engage, in a fluidly sealed manner, said second end of said housing;

b. engaging said first end of said housing to valve engaging a pressurized vessel containing a pressurized fluid process;

c. opening said valve, providing an opening;

d. allowing said pressurized fluid process to selectively pass through said opening in said valve, and into said internal cavity formed in said housing;

e. extending said first end of said probe from said housing, through said open valve, into said pressure vessel, such that said first end of said probe engages said pressurized fluid process;

f. retracting said probe into said housing, and g. closing said valve.

2. The method of claim 1, wherein there is provided the further step in step "a" the additional step of mounting a sensor to said first end of said probe, and in step "e" of exposing said sensor to said pressurized fluid process.

3. The method of claim 1, wherein there is further provided in step "a" the additional step of mounting a closed end cap having a cavity to said first end of said probe, such that said cavity of said closed end cap communicates with said passage formed in said probe, to provide a well, and in step "e" there is provided the additional step of lowering a sensor into said well while said well remains at atmospheric pressure with said probe engaging said pressurized vessel to seal said well from said pressurized fluid process, allowing said sensor to analyze said pressurized fluid process, while remaining at atmospheric pressure.

4. The method of claim 1, wherein in step "e" there is further provided the additional step "e1" of allowing said pressurized fluid process to flow into said conduit formed in said probe, sampling said pressurized fluid process, providing sampled fluid.

5. The method of claim 4, wherein in step "a" there is further provided the step providing a flexible conduit having first and second ends, said first end engaging said second end of said probe, said second end of said conduit engaging said outlet port of said housing assembly, to provide fluid communication therebetween, and in step "e" there is further provided the step "e2" of directing said sampled fluid through said flexible conduit, through the outlet port of said housing assembly, for collection.

6. The method of claim 4, wherein in step "a" there is further provided the step of providing a phase separating membrane/filter assembly engaging said first end of said probe, and in step "e" there is further provided the step "e2" of utilizing said phase separating membrane/filter assembly to engage said pressurized process fluid such that gas flows through said phase separating membrane/filter assembly into said conduit formed in said probe, while rejecting liquid and solid particles flowing through said pressurized process fluid.

7. The method of claim 1, wherein there is provided the further step in step "a" the additional step of mounting a corrosion coupon to said first end of said probe, and in step "e" of exposing said corrosion coupon to said pressurized fluid process.

8. The method of claim 1, wherein there is provided the further step in step "a" the additional step of mounting a sensor to said first end of said probe, and in step "e" of utilizing said sensor to analyze said pressurized fluid process.

9. The method of engaging a pressurized fluid system with a probe, comprising the steps of:

a. providing a probe housing assembly for insertion and retraction of a probe into a pressurized vessel, comprising:

a probe having first and second ends, said probe having an internal fluid passage formed therethrough extending from said first end of said probe to said second end of said probe:

a housing having first and second ends, said housing having an internal cavity formed therethrough extending from said first end of said housing to said second end of said housing, said housing formed to engage, in a fluidly sealed manner, a pressurized fluid process in said pressurized vessel, said probe slidingly disposed in said internal cavity formed in said housing in an approximate coaxial relationship with said housing, such that said second end of said probe can engage, in a fluidly sealed manner, said housing;

b. engaging said first end of said housing to a valve engaging a pressurized vessel containing a pressurized fluid process;

c. opening said valve, providing an opening;

d. allowing said pressurized fluid process to selectively pass through said opening in said valve;

e. extending said first end of said probe from said housing, through said open valve, into said pressure vessel, such that said first end of said probe engages said pressurized fluid process;

f. retracting said probe into said housing, and closing said valve.

10. The method of engaging a pressurized fluid system with a probe, comprising the steps of:

a. providing a probe housing assembly for insertion and retraction of a probe into a pressurized vessel having an exterior, comprising:

a probe having first and second ends and a length, said probe having an internal fluid passage formed therethrough extending from said first end of said probe to said second end of said probe:

a housing having first and second ends, said housing having an internal cavity formed therethrough extending from said first end of said housing to said second end of said housing, said housing formed to engage, in a fluidly sealed manner, a pressurized fluid process in said pressurized vessel, said probe slidingly disposed in said internal cavity formed in said housing in an approximate coaxial relationship with said housing;

b. positioning said length of said probe within said housing;

c. engaging said first end of said housing to the exterior of a pressurized vessel containing a pressurized fluid process;

d. allowing said pressurized fluid process to migrate into said housing from said pressurized vessel until there is pressure equalization between said housing and said pressurized vessel;

e. extending said first end of said probe from said housing, into said pressure vessel, such that said first end of said probe engages said pressurized fluid process;

f. allowing said pressurized fluid process to flow through said probe; and g. retracting said probe until the length of said probe is situated in said housing.

11. The method of claim 10, wherein in step "b" there is provided the additional step of providing a valve situated between said first end of said housing and said pressurized vessel.

12. The method of claim 11, wherein after step "b" there is further provided the additional step "b1" of opening said valve, providing an opening.

13. The method of claim 12, wherein in step "c" said first end of said probe is extended through said opening in said valve.

14. The method of claim 13, wherein after step "d" there is further provided the additional step "d1" of closing said valve.

15. The method of claim 10, wherein after step "b" there is further provided the step of providing an opening between said housing and said pressurized vessel to allow said pressurized fluid process, and wherein in step "c" said first end of said probe is extended through said opening into said pressurized fluid process, and wherein after step "d" there is provided the further step "d1" of closing said opening.

* * * * *